United States Patent [19]

Khanna et al.

[11] Patent Number: 5,573,955
[45] Date of Patent: Nov. 12, 1996

[54] REDUCING TYRAMINE INTERFERENCE IN IMMUNOASSAYS FOR AMPHETAMINE AND METHAMPHETAMINE

[75] Inventors: Pyare Khanna, Fremont; Theresa Medlin, San Ramon, both of Calif.

[73] Assignee: Microgenics Corp., Concord, Calif.

[21] Appl. No.: 465,366

[22] Filed: Jun. 5, 1995

[51] Int. Cl.$^6$ .................................................. G01N 33/53
[52] U.S. Cl. .......................... 436/501; 435/7.1; 435/7.9; 435/7.92; 435/7.93; 435/7.94; 435/7.95; 435/191; 435/228; 435/962; 436/545; 436/175; 436/816; 436/822; 436/825; 436/901
[58] Field of Search ................ 435/7.1, 7.9, 7.92–7.95, 435/212, 228, 191, 962; 436/501, 545, 175, 816, 822, 825, 901

[56] References Cited

U.S. PATENT DOCUMENTS

| | | | |
|---|---|---|---|
| 3,856,469 | 12/1974 | Schneider et al. | 435/7.1 |
| 3,878,187 | 4/1975 | Schneider et al. | 260/121 |
| 3,996,344 | 12/1976 | Gross | 424/1.5 |
| 4,016,146 | 4/1977 | Soares | 436/501 |
| 4,041,076 | 8/1977 | Avenia et al. | 436/501 |
| 4,329,281 | 5/1982 | Christenson et al. | 260/112 |
| 4,496,655 | 1/1985 | Yoshino et al. | 435/191 |
| 4,668,620 | 5/1987 | Armenta et al. | 435/7 |
| 4,868,132 | 9/1989 | Byrnes et al. | 436/546 |
| 5,101,015 | 3/1992 | Brynes et al. | 530/363 |
| 5,135,863 | 8/1992 | Hu et al. | 435/188 |
| 5,248,791 | 9/1993 | Brynes et al. | 549/223 |
| 5,262,333 | 11/1993 | Heiman et al. | 436/537 |

OTHER PUBLICATIONS

Database Derwent WPI on Dialog, week 9027, London: Derwent Info. Ltd., AN 90–209876, C. H. Self, "Homogeneous, non–competitive assay for small analytes–using prim. binding partner associated with member of signal generating pair," WO 9006512 published 14 Jun. 1990.

CEDIA® DAU Amphetamine, (Microgenics Corp., Concord CA) package insert No. 98–961–0, Dec. 1984.

Cheng et al., "Amphetamines: New Radioimmunoassay", FEBS Letters 36:3 (1973) pp. 339–342.

Inayama, et al., "Preparation of a Specific Antibody to Methamphetamine" Chem. Pharm. Bull. 25(4): (1977) pp. 838–840.

Aoki, et al., "A Screening Method for Urinary Methamphetamine–Latex Agglutination Inhibition Reaction Test" Forensic Science International 27: (1985) pp. 49–56.

Halfman, et al., "Homogeneous, Micelle Quenching Fluoroimmunoassay for Detecting Amphetamines in Urine" Clin. Chem. 32(9): (1986) pp. 1677–1681.

Tamaki, et al., "Solid–Phase MicroELISA for Methamphetamine" Jpn J. Legl Med. 37(4): (1983) pp. 417–420 (page 420 in Japanese).

Inayama, et al "The Radioimmunoassy for Methamphetamine" Chem. Pharm. Bull. 25(4): (1977) pp. 840–842.

Budd, "Amphetamine EMIT—Structure Versus Reactivity" Clin. Toxicology 18(1): (1981) pp. 91–110.

*Primary Examiner*—Carol A. Spiegel
*Attorney, Agent, or Firm*—Luann Cserr

[57] ABSTRACT

A method for reducing or eliminating tyramine interference from amphetamine and methamphetamine immunoassays, comprising treating the sample with aqueous tyramine oxidase for a time and at a temperature and pH sufficient to deaminate any tyramine present in the sample, is provided.

7 Claims, No Drawings

REDUCING TYRAMINE INTERFERENCE IN IMMUNOASSAYS FOR AMPHETAMINE AND METHAMPHETAMINE

BACKGROUND

1. Technical Field

Background interference can be a serious factor in diminishing the quantitative character of an immunoassay. In many situations, the background interference will vary from sample to sample and will be different in the analyte-containing samples than in the standards or calibrators employed for translating the observed signal into the concentration of the analyte. To enhance assay accuracy, it is desirable to diminish or remove the background interference contributed to the observed signal during the immunoassay.

This disclosure relates in particular to diminishing or removing background interference in immunoassays for the detection of amphetamine and methamphetamine, specifically interference caused by tyramine.

2. Background Art

Amphetamine and methamphetamine, the structural chemical formulas of which are presented below, are sympathomimetic phenethylamine derivatives having central nervous system stimulant activity.

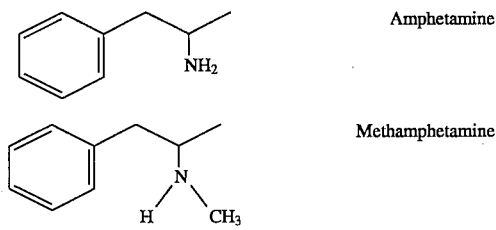

They have been used for the treatment of obesity, narcolepsy, and hypotension. However, excessive or prolonged use may lead to tolerance and physical dependence. Because of their stimulant effects, these drugs are commonly sold illicitly. Physiological symptoms associated with high amounts of ingested amphetamine and methamphetamine include elevated blood pressure, dilated pupils, hyperthermia, convulsions, and acute amphetamine psychosis.

The biological fluid tested most frequently for the presence of amphetamine and methamphetamine is urine. Such substances have been detected by a number of techniques, including, for example, thin layer chromatography, gas chromatography, and high performance liquid chromatography. These methods require chemical extractions of the drugs from the urine sample, necessitating the use of labor intensive procedures requiring highly trained personnel and lengthy assay times.

For these reasons, immunoassays are a preferable alternative. Typically, in an immunoassay, for example, a competitive binding immunoassay, an analyte (a substance of biological interest to be determined quantitatively) competes with a labeled reagent, i.e. "an analyte analog," for a limited number of receptor binding sites on antibodies specific to the analyte and the analyte analog. The concentration of analyte in the sample determines the amount of analyte analog that binds to the antibody. The amount of analyte analog that binds to the antibody is inversely proportional to the concentration of analyte in the sample, because the analyte and the analyte analog each bind to the antibody in proportion to their respective concentrations.

An accurate and reliable immunoassay for amphetamine and d-methamphetamine requires that antibody "cross-reactivity" (i.e., recognition of compounds other than the desired analyte) be minimized. Although the d- and l-enantiomers of methamphetamine are controlled substances in the United States, the l-enantiomer has weaker stimulant activity and is contained in small amounts in some prescription and over-the-counter medications. It is therefore undesirable for an assay (in particular one employed to detect drug abuse) to respond to l-methamphetamine alone in a sample. Therefore, the cross-reactivity for l-methamphetamine should ideally be zero. Since l-amphetamine is a major metabolite of l-methamphetamine, it is also undesirable for the assay to respond to l-amphetamine. Ideally, the assay will be specific for the d-enantiomers of both amphetamine and methamphetamine.

Other cross-reacting compounds, for example, derivatives of β-hydroxyphenethylamine compounds, are known interferants in amphetamine and methamphetamine immunoassays. One such β-hydroxyphenethylamine, phenylpropanolamine, is found frequently in decongestants and diet pills sold over the counter. U.S. Pat. No. 3,856,469 discloses removal of β-hydroxyphenethylamine interference from a sample intended for amphetamine and/or methamphetamine analysis by treating the sample at a pH greater than 8.0 with an amount of aqueous periodate in the presence of ammonium hydroxide.

In addition, tyramine, which may be present naturally in a biological sample being analyzed for amphetamine and/or methamphetamine, may also be a strong interferant. Tyramine, p-hydroxyphenylethylamine, is a decarboxylation product of tyrosine, an amino acid found in most proteins. Tyramine interference from endogenous tyramine in an immunoassay can produce false positive results. The compositions and methods of the present invention significantly improve the selectivity of assays for d-amphetamine and d-methamphetamine (hereinafter alternatively termed amphetamine-class compounds or analytes) over tyramine in comparison with prior art methods.

For art relating to the detection of amphetamine and methamphetamine in biological samples, U.S. Pat. Nos. 3,996,344 and 4,016,146 (disclosing phenethylamine antigenic conjugates, their preparation, antibodies and use); 4,041,076 (disclosing immunoassay for pharmacologically active phenothylamines); 4,329,281 (disclosing hapten compositions for making immunogens usable to elicit antibodies selective to amphetamine and methamphetamine); 3,878,187 (disclosing polypeptide derivative amphetamine analogs for immunoassays); 5,101,015, 5,248,791, and 5,262,333 (disclosing reagents for use in fluorescence polarization immunoassay for amphetamine-class analyte detection) are exemplary. In addition, the scientific literature discloses a variety of amphetamine detection methodologies and reagents. See, for example, FEBS LETTERS 36:3 (1973) disclosing a radioimmunoassay procedure for measuring amphetamines in urine); Chem. Pharm. Bull. 25(4):840 (1977) (disclosing another radioimmunoassay for methamphetamine); Forensic Science International 27:49 (985) (disclosing a latex agglutination inhibition reaction test for screening urinary amphetamine); Clin. Chem. 32(9):1677 (1986) (disclosing a homogeneous fluoroimmunoassay for detecting amphetamines in urine; Jpn J. Legal Med. 37(4):417 (1983) (disclosing a solid phase micro-ELISA for methamphetamine); Chem. Pharm. Bull. 25(4):838 (1977) (disclosing preparation of a specific antibody to methamphetamine); and Clinical Toxicology, 18(1):91 (1981) (disclosing the analysis of amphetamine-related amines by the "EMIT"™ procedure).

For art relating to reducing background interference in immunoassays generally, U.S. Pat. No. 4,668,620 (treatment of serum samples with peracids or persulfates to reduce interference caused by serum components other than analytes), U.S. Pat. Nos. 3,856,469 (use of periodate to reduce interference from β-hydroxyphenethyl amines) and 5,262,333 (use of periodate to treat urine samples to reduce, inter alia, tyramine interference in immunoassays) are exemplary.

SUMMARY OF THE INVENTION

Compositions and methods are provided for diminishing or eliminating endogenous tyramine background interference in urine samples, which will be subjected to an assay for the determination of amphetamine-class analytes. The reduction in background interference is greater than about 10%, more usually greater than about 50%, and preferably about 100%.

Tyrosine is an amino acid which is found in most proteins and which is synthesized metabolically from phenylalanine. Tyramine (p-hydroxyphenylethylamine) is a decarboxylation product of tyrosine and is excreted in urine. It is a component of some foods, such as cheese, and is a product of bacterial degradation. It has the structural chemical formula presented below.

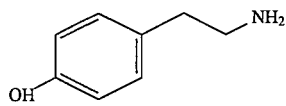

Even a small amount of tyramine cross-reactivity (for example 1–2%) may result in a false positive result if a urine sample contains a substantial amount of tyramine. Consequently, an accurate and reliable immunoassay for amphetamine-class analytes (i.e., d-amphetamine and d-methamphetamine) requires that antibody cross-reactivity with tyramine be minimized. It was unexpectedly found that the addition of tyramine oxidase to the immunoassay significantly improves the selectivity of the immunoassay for d-amphetamine and d-methamphetamine over tyramine in comparison with those methods described in the art.

Tyramine oxidase is a bacterial enzyme in the genus Arthrobacter that deaminates tyramine at the α carbon to yield p-hydroxybenzaldehyde, hydrogen peroxide and ammonia, as shown below.

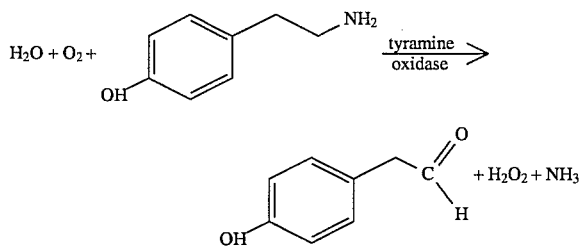

It has previously found use in clinical assays for leucine aminopeptidase activity. See U.S. Pat. No. 4,496,655. It is available from the Fermentation Institute, Agency of Industrial Technology and Science, MITI, Japan as culture collection FERM-P No. 6240. It is also available from Sigma Chemical Co. Cat. No. T0905. Although in the practice of the invention the above-mentioned strains can be used, the invention is not limited to these strains. Other tyramine-oxidase-producing strains of the genus Arthrobacter can be readily isolated by one reasonably skilled in the art and used in the method of this invention.

Accordingly, in one embodiment, the invention comprises a method for reducing tyramine-caused background interference in immunoassays by incorporating into the sample a tyramine-reducing amount of tyramine oxidase under conditions sufficient to reduce such tyramine-caused interference. In the method, the medium to be assayed is combined with a small amount of an aqueous tyramine oxidase solution at ambient temperature and neutral pH for sufficient time to deaminate any tyramine in the medium so as to destroy its interfering effect. The sample is then used in the determination of amphetamine-class analytes. The method finds particular use in immunoassays. In another embodiment, the invention comprises a reagent kit useful in the detection of amphetamine-class analytes in a biological fluid sample. In yet another embodiment, the invention includes a tyramine-reducing assay treatment solution comprising an aqueous solution of tyramine oxidase having a concentration in the range of $1 \times 10^{-4}$ to 10 units/mL and a pH from about 5.0 to 10.0. Preferably, the solution includes 0.001 to 10 units/mL of tyramine oxidase having a pH range from about 6.0 to 8.0. One unit of tyramine oxidase activity is defined herein as that amount which will oxidize 1.0 μmole of tyramine to p-hydroxyphenylacetaldehyde per minute at pH 7.5 at 37° C. Surprisingly, it has been found that tyramine oxidase selectively deaminates tyramine, leaving the amphetamine-class analytes in the sample available for detection.

DETAILED DESCRIPTION OF SPECIFIC EMBODIMENTS

Methods and compositions are provided for diminishing or eliminating background interference from tyramine in urine samples, which will be subjected to an assay for the determination of analytes, particularly, but not necessarily, where measurement of enzyme activity is employed. The reduction in background interference is greater than about 10%, more usually greater than about 50%, and preferably about 100%.

In the method, the urine sample is treated with an effective amount of aqueous tyramine oxidase solution having a pH of about 5 to 10 for a period of time sufficient to render any tyramine present in the sample unreactive with the antibody reagent, i.e. to eliminate undesired tyramine cross-reactivity. Preferably, the sample is treated with 0.001 to 10 units/mL of aqueous tyramine oxidase solution for about 5 to 180 minutes, most preferably 45° to 180 minutes at a temperature range from about 15 to 40° C.

The method is particularly useful in enzyme complementation assays, where a medium suspected of containing an analyte is combined with (1) a conjugate, comprising an enzyme fragment (termed an enzyme donor), and an analyte, (2) a receptor for the analyte, typically an antibody specific to the analyte, (3) another enzyme fragment (termed an enzyme acceptor) capable of combining with the enzyme donor-analyte conjugate to form an active, detectable, enzyme, and (4) a substrate upon which the enzyme can act. The effect of the combination on the enzymatic activity of the conjugate is measured and compared to the effect obtained using samples containing known amounts of analyte to determine the presence and amount of analyte in the sample. Such assays as are disclosed in U.S. Pat. Nos. 4,708,929, 5,212,064 and 4,378,428 are exemplary. Alternatively, the method is also useful in fluorescence polarization immunoassays such as those disclosed in U.S. Pat. No.

5,262,333, in "dip-stick" immunoassays such as those disclosed in U.S. Pat. No. 4,444,880 and in enzyme immunoassays employing whole enzyme, such as those disclosed in U.S. Pat. No. 4,668,620.

The amount of tyramine oxidase employed per milliliter of sample may be varied widely, depending upon the activity of the oxidase, the period of treatment as well as the degree of reduction in endogenous tyramine concentration desired. The amount of tyramine oxidase employed will generally be at least about $1\times10^{-4}$ units per ml (i.e., at least about $6.9\times10^{-13}$ mole per ml of sample), more usually about 0.001–1 units/mL (i.e., $6.9\times10^{-12}$ mole to $6.9\times10^{-9}$ mole per ml of sample). The concentration of the oxidase during the incubation with the sample will also vary widely, generally ranging from at least 0.1 units/L (i.e., at least $6.9\times10^{-10}$) and up, more usually from about 1 to about 1000 units/L (i.e., about $6.9\times10^{-9}$M to about $6.9\times10^{-6}$M). The pH will normally be about 4 to 10, more usually from about 6 to 8.

Various buffers may be employed, such as borate, phosphate, glycine, carbonate, Tris, and the like. When buffer is employed, the concentration of buffer may vary widely, but should be sufficient to maintain the desired pH. Usually, buffer concentrations will generally be from about 0.025 to 0.5M, more usually about 0.1 to 0.2M. The concentration of buffer is not critical.

The treatment method requires combining the sample, the tyramine oxidase, conveniently as an aqueous solution, and, as desired, buffer. The sample may be subjected to prior treatment, such as filtration, centrifugation, or the like. The tyramine oxidase may be added as its salt. The combined sample and oxidase will then be incubated for at least about 5 min., usually not more than about 4 hrs., preferably from about 45 min to 3 hr., more usually from about 45 to 60 min. at a temperature of about 15° to 40° C., preferably 20° to 37° C. The particular incubation time, once past the minimum time, is a matter of convenience, and will vary in relation to the amount of oxidase used, the amount of components contributing to the background interference, the incubation temperature, the rate at which these components are rendered inactive by interaction with the oxidase, and the stability of analyte.

The various volumes employed will be determined by the permissible dilution of the urine sample. Therefore, the particular concentrations employed, the ratios of volumes of urine, oxidase and buffer will all be related to the final volume of the assay sample and the desired concentration of the urine in the sample. Usually, about 5 to 20 microliters of oxidase will be used per 200 microliters of urine.

The materials are combined and agitated in order to insure substantially uniform dispersion, and the mixture incubated at ambient temperatures for the indicated period of time. After the treatment, the assay may then be made directly on the sample by adding whatever appropriate reagents are required for the assay determination.

In a variant of the above method, the tyramine oxidase may be incorporated directly into the reagent(s) of the immunoassay used for detecting amphetamine-class compounds in such a way as to allow the tyramine oxidase to reduce or eliminate the tyramine from the sample prior to the completion of the assay determination for that sample. This method requires combining tyramine oxidase with one or more of the reagents used in the assay rather than pretreating the samples prior to reagent addition. The tyramine oxidase may be added, either in the form of an aqueous solution or its salt, such that the amount of tyramine oxidase reacting with the sample during the assay determination is similar to the amounts previously described. After incorporation of tyramine oxidase into the reagent(s) of the assay, the assay determination can be conducted as recommended by the manufacturer.

The following examples are offered to illustrate (without limiting) the invention.

EXAMPLES

All temperatures are in centigrade. All parts and percents not otherwise indicated are by weight, except that liquid mixtures are by volume. All solutions are aqueous unless otherwise indicated.

EXAMPLE 1

Variable amounts of tyramine oxidase (Sigma Chemical Co. Cat. No. T0905) were added to urine samples to which known amounts of tyramine had been added. After either 45 min. or 180 min., the samples were run in a CEDIA® homogeneous enzyme complementation assay for amphetamine-class analytes (Microgenics Corp., Concord, Calif.) following the protocol of the package insert. The apparent amphetamine dose was then calculated from a series of amphetamine standards and is shown in ng/mL in the following table.

SAMPLE PRE-TREATMENT WITH TYRAMINE OXIDASE

| 45 minutes pre-treatment at 20° C., pH 7.0 | | | | | | | |
|---|---|---|---|---|---|---|---|
| [Tyramine], ng/mL added to Sample | 0 | 1000 | 5000 | 10000 | 50000 | 100000 | 500000 |
| [Tyramine Oxidase] units/mL, in the sample | Apparent Amphetamine Concentration (ng/mL) as measured by Immunoassay | | | | | | |
| 0 | 52 | 106 | 244 | 453 | 1476 | 2540 | >3000 |
| 0.0001 | 17 | 73 | 241 | 419 | 1395 | 2440 | >3000 |
| 0.001 | 45 | 56 | 50 | 228 | 1160 | 2287 | >3000 |
| 0.01 | 32 | 50 | 62 | 19 | 107 | 775 | >3000 |
| 0.1 | 42 | 28 | 42 | 33 | 47 | 47 | 1863 |

| 180 Minutes Pre-Treatment at 20° C., pH 7.0 | | | | | | | |
| --- | --- | --- | --- | --- | --- | --- | --- |
| [Tyramine], ng/mL added to Sample | 0 | 1000 | 5000 | 10000 | 50000 | 100000 | 500000 |
| [Tyramine Oxidase], units/mL, in the sample | Apparent Amphetamine Concentration (ng/mL) as measured by Immunoassay | | | | | | |
| 0 | 48 | 46 | 238 | 401 | 1640 | 2504 | >3000 |
| 0.0001 | 21 | 54 | 172 | 379 | 1400 | 2322 | >3000 |
| 0.001 | 13 | −3 | 33 | −4 | 963 | 2161 | >3000 |
| 0.01 | 15 | −12 | 5 | 11 | 20 | 78 | >3000 |
| 0.1 | 16 | −17 | −13 | 13 | 12 | −2 | 690 |

This experiment demonstrated that the addition of tyramine oxidase directly to the sample would reduce the assay's response to tyramine in a urine sample. As a comparison of the results between the two incubation times indicates, the majority of the reduction in the tyramine concentration occurs during the first 45 minutes of pre-treatment. The additional incubation time at the 3 hour condition impacted only the very highest concentration samples.

EXAMPLE 2

In this experiment, variable amounts of tyramine oxidase were added by inclusion in the first reagent of a CEDIA homogeneous enzyme complementation assay, rather than as a separate pretreatment. The reagents were then used following the package protocol to determine the apparent amphetamine concentration in several samples to which known amounts of tyramine had been added. The apparent amphetamine dose was calculated from a series of amphetamine standards and is shown in ng/mL in the following table. The assay procedure consisted of combining the CEDIA enzyme acceptor (EA) reagent, containing the EA protein and antibody to amphetamine with variable amounts of tyramine oxidase, in a buffer solution at pH 6.9. The sample/reagent mixture was mixed and incubated for 5 minutes at 37° C. After the 5 min incubation, the enzyme donor reagent (R2), containing the enzyme donor (ED) conjugate and substrate in a buffer solution were combined with the EA/sample mixture. After mixing, this solution was incubated for 5 min at 37° C. The results were read on a HITACHI™ 717 Analyzer 15 (Boehringer-Mannheim, Indianapolis, Ind.).

| Elimination of Tyramine by Tyramine Oxidase in the R1 Reagent | | | | | | | | |
| --- | --- | --- | --- | --- | --- | --- | --- | --- |
| [Tyramine], ng/mL | 0 | 1000 | 5000 | 10000 | 50000 | 100000 | 500000 | 1000000 |
| [Tyramine Oxidase], Units/ML, in the first incubation with sample | Apparent Amphetamine Concentration (ng/mL) as measured by Immunoassay | | | | | | | |
| 0.0 | 63 | 100 | 281 | 434 | 1500 | 2422 | >5000 | >5000 |
| 0.005 | 16 | 84 | 249 | 383 | 1247 | 2044 | >5000 | >5000 |
| 0.01 | 79 | 90 | 202 | 352 | 1058 | 1957 | >5000 | >5000 |
| 0.05 | 12 | 36 | 41 | 65 | 367 | 784 | >5000 | >5000 |
| 0.1 | 30 | 28 | 25 | 46 | 51 | 162 | 2268 | >5000 |
| 0.5 | 8 | 26 | 14 | 26 | 4 | 9 | 18 | 15 |
| 1.0 | 16 | 13 | 25 | 34 | 11 | 12 | 0 | −17 |

This experiment demonstrated that the tyramine oxidase when added to the first reagent effectively removed tyramine from urine samples containing tyramine after a five minute incubation at 37° C.

EXAMPLE 3

Using the same reagents as in Example 2, seven samples that gave a dose response greater than 700 ng/mL in the assay but contained less than 500 ng/mL amphetamine by GC/MS analysis were evaluated to determine if the dose response would be affected by the addition of variable amounts of tyramine oxidase to the first reagent. Incubation temperature was 37° C., pH was 6.9 and time of incubation was 5 minutes. Results were read in a HITACHI™ 717 Analyzer (Boehringer-Mannheim, Indianapolis, Ind.).

| Elimination of Tyramine by Tyramine Oxidase in the R1 Reagent | | | | | | | |
| --- | --- | --- | --- | --- | --- | --- | --- |
| GC/MS Sample # | 37 | 66 | 205 | 214 | 217 | 244 | 279 |
| Result | CNF | CNF | CNF | CNF | CNF | CNF | CNF |
| [Tyramine Oxidase], units/mL, in the first incubation with sample | (CNF = Compound not found) Apparent Amphetamine Concentration (ng/mL) as measured by Immunoassay | | | | | | |
| 0.0 | 762 | 831 | 1027 | 1678 | 839 | 924 | 696 |
| 0.005 | 671 | 690 | 893 | 1345 | 713 | 774 | 632 |
| 0.01 | 616 | 672 | 858 | 1240 | 661 | 756 | 616 |
| 0.05 | 243 | 217 | 310 | 486 | 238 | 323 | 298 |
| 0.1 | 106 | 61 | 74 | 241 | 70 | 159 | 162 |
| 0.5 | 91 | −1 | −8 | 122 | 7 | 130 | 149 |
| 1.0 | 67 | −4 | −11 | 148 | 7 | 68 | 155 |

This experiment indicated that the tyramine oxidase incorporated into the first reagent reduced the apparent concentration of amphetamine in samples containing tyramine.

EXAMPLE 4

Using the same reagents as in Examples 2 and 3, a test of d-amphetamine and d-methamphetamine controls indicated that tyramine oxidase addition had no significant impact on the concentration of d-amphetamine and d-methamphetamine in the sample. Urine samples containing either 750 ng/mL or 1250 ng/mL of d-amphetamine or d-methamphetamine were run in a CEDIA® homogeneous enzyme complementation assay (Microgenics Corp., Concord, Calif.) following the protocol of the package insert, except that, as in Examples 2 and 3, variable amounts of aqueous tyramine oxidase were added by inclusion in the first reagent.

Elimination of Tyramine by Tyramine Oxidase in the R1 Reagent

Temp of incubation: 37° C. Instrument: Hitachi 717
Time of incubation: 5 minutes pH of reaction: 6.9

| Sample | d-Amphetamine | | d-Methamphetamine | |
|---|---|---|---|---|
| | $C1 =$ 750 ng/mL | $C2 =$ 1250 ng/mL | $C1 =$ 750 ng/mL | $C2 =$ 1250 ng/mL |
| [Tyramine Oxidase], units/mL, in the first incubation | Apparent Amphetamine Concentration (ng/mL) as measured by Immunoassay | | | |
| 0.000 | 546 | 1325 | 692 | 1346 |
| 0.005 | 517 | 1296 | 683 | 1331 |
| 0.010 | 530 | 1290 | 701 | 1359 |
| 0.050 | 542 | 1290 | 710 | 1327 |
| 0.100 | 520 | 1322 | 699 | 1333 |
| 0.500 | 523 | 1303 | 689 | 1368 |
| 1.000 | 534 | 1315 | 706 | 1341 |

It will be apparent to one of ordinary skill in the art that many changes and modifications can be made to the invention without departing from the spirit or scope of the appended claims.

What is claimed is:

1. In an immunoassy method for determining amphetamine or methamphetamine in a biological sample suspected of containing said amphetamine or methamphetamine, wherein any tyramine present in said sample would interfere with said determination, the improvement comprising treating said sample with an amount of tyramine oxidase sufficient to reduce interference from said tyramine in said immunoassay.

2. The method of claim 1 wherein said tyramine oxidase is added to said sample prior to performing said immunoassay.

3. The method of of claim 1 wherein said amount of tyramine is at least about $1 \times 10^{-4}$ units/ml of said sample.

4. The method of claim 1 wherein the pH of a mixture of said tyramine oxidase and said sample is in the range of about 4 to 10.

5. The method of claim 1 wherein treating said sample is carried out at a temperature in the range of about 15° to 40° C. for a time in the range of about 5 minutes to 4 hours.

6. In a for carrying out an immunoassay to detect amphetamine or methamphetamine in a sample, the improvement comprising
treating said sample to be assayed with an amount of tyramine oxidase inthe range of about $1 \times 10^{-4}$ to 10 units/ml of said sample.

7. The method of claim 6 wherein said tyramine oxidase is added to said sample prior to carrying out said immunoassay.

* * * * *